(12) United States Patent
Mangan

(10) Patent No.: US 6,381,750 B1
(45) Date of Patent: May 7, 2002

(54) HEADGEAR MOUNTABLE SHIELD AND METHOD OF USE

(76) Inventor: Norman B. Mangan, 1468 Balboa Ave., Burlingame, CA (US) 94010

(*) Notice: Subject to any disclaimer, the term of this patent is extended or adjusted under 35 U.S.C. 154(b) by 0 days.

(21) Appl. No.: 09/963,003

(22) Filed: Sep. 25, 2001

(51) Int. Cl.[7] ................................. A61F 9/00
(52) U.S. Cl. ................................. 2/10; 2/207
(58) Field of Search .................. 2/172, 209.13, 2/175.6, 10, 15, 9, 6.7, 424, 6.3, 207

(56) References Cited

U.S. PATENT DOCUMENTS

| | | | | |
|---|---|---|---|---|
| 1,285,109 A | * | 11/1918 | Friedman | 2/10 |
| 1,955,232 A | * | 4/1934 | Gallaway | 2/10 |
| 3,346,876 A | * | 10/1967 | Hutton | 2/10 |
| 3,551,910 A | * | 1/1971 | Raschke | 2/415 |
| 3,613,115 A | * | 10/1971 | Hill | 2/10 |
| 3,668,706 A | * | 6/1972 | Velasquez | 2/10 |
| 3,946,466 A | * | 3/1976 | Sakai | 2/10 |
| 4,224,694 A | * | 9/1980 | Palmaer | 2/422 |
| 4,547,908 A | * | 10/1985 | Karlsson et al. | 2/10 |
| 4,821,341 A | * | 4/1989 | Baptiste | 2/10 |
| 4,928,324 A | * | 5/1990 | Evans et al. | 2/10 |

* cited by examiner

*Primary Examiner*—Rodney M. Lindsey
(74) *Attorney, Agent, or Firm*—Ted Masters

(57) ABSTRACT

A shield for protecting a wearer from ultraviolet radiation is removably attachable to headgear such as a hard hat, helmet, baseball cap and the like. The shield attaches to the visor or bill of the headgear, wraps around the headgear, and is connected at the back of the headgear, thereby protecting the face and neck of a wearer. The shield has a clamp, which in a preferred embodiment, attaches to the center of the visor of the headgear. In another embodiment of the invention, the shield filter includes a curtain which attaches to the sides of the shield and wraps around the back of the headgear and hangs down to also protect the sides and back of the wearer's neck.

12 Claims, 6 Drawing Sheets

HEADGEAR MOUNTABLE SHIELD AND METHOD OF USE

TECHNICAL FIELD

The present invention pertains generally to devices which protect a wearer from the harmful effects of ultraviolet radiation from the sun, and more particularly to a flexible shield which can be attached to and wrapped around the hat or other headgear of the wearer.

BACKGROUND OF THE INVENTION

Many people have skin which is sensitive to the sun's powerful rays. Even when these people use the most protective sun block products, they can still burn after only a short period of exposure. One solution to this problem is to shield the face and neck of the individual with a material which blocks the harmful ultraviolet light, but which passes visible light. Such shields, facemasks, and the like, which attach to headgear, and which protect a user, are well known in the art. For example:

U.S. Pat. No. 4,884,296 shows a protective face shield having a shield member of transparent flexible material in the upper corners of which pairs of slits are formed. A headband is threaded through the slits in a manner such that once the headband is donned the shield member may be pulled away from the wearer's face to provide good air circulation. A lower portion of the face shield is contoured inwardly to protect the throat.

U.S. Pat. No. 5,544,361 illustrates a lightweight headgear mountable protective face shield capable of protecting substantially the entire face of a human wearer from ultraviolet radiation. The face shield comprises an articulated shielding arrangement to be positioned in blocking relationship to tie wearer's face. The shielding arrangement comprising a plurality of segments extending across the wearer's face, the ends of which are preferably pivotally connected to hinge plates positioned at either side of the wearer's head. The hinge plates are attached to a securing mechanism which secures the face shield to an article of headgear. In a preferred embodiment, the face shield is detachably secured to the forwardly projecting bill of a baseball style cap by a securing mechanism comprising a pair of jaws between which the bill is secured by clamping.

U.S. Pat. No. 5,634,210 discloses a flexible face shield which includes two side wings that are connected to a main body by living hinges and a face-engaging element that spaces the body away from the face of a wearer. A flexible band attaches the shield to the wearer. The face shield body is opaque to the sun and one form of the shield includes cutouts which are covered with sunglasses-type material. The body is preferably cardboard or other such material so the shield can be folded and bent for storage or to customize it for the particular wearer. The shield can be discarded after use if desired.

U.S. Pat. No. 5,806,102 is directed to a face shield for a helmet. The face shield having a weather lens and a face lens spaced from the weather lens so as to form an air gap, is characterized in that an electroconductive film is attached to the air gap of the weather lens, in that upper and lower electrodes are printed on upper and lower sides of the electroconductive film, respectively, in that a plurality of dot electrodes which are uniformly spaced from each other are printed on the entire part of the electroconductive film, and in that the weather lens is made from a material such as a polycarbonate, butyrate, or an acrylic, and the face lens from an anti-fog sheet.

SUMMARY OF THE INVENTION

The present invention is directed to a darkly tinted shield which removably attaches to a hat or other headgear to protect the face and neck of a wearer from the harmful effects of ultraviolet radiation from the sun. A preferred name for the present invention is "Daisy Shader".

In a preferred embodiment of the invention, a shield for protecting the face and neck of a wearer from ultraviolet radiation is mountable in wrap around fashion to headgear such as a hat, a helmet, a cap, and the like. The shield is attached to the center of the visor or brim of the headgear, and wraps around both sides of the headgear fastening in the back of the headgear. The shield includes a thin sheet which blocks much of the ultraviolet radiation but passes visible light so that the wearer can see. The sheet is shaped and dimensioned so that when it is wrapped around the headgear, it covers the face of the wearer. Elastic straps are connected to each end of the sheet so that the straps may be wrapped around the headgear and connected at the back of the headgear, thereby attaching the shield to the headgear. A clamp is disposed near the top center of the sheet. The clamp is shaped and dimensioned to receive and selectively grasp the visor of the headgear, so that the clamp may be fixedly attached to the center of the visor. The clamp is designed to permit the shield to be mounted flush with the visor of the headgear.

In accordance with an important aspect of the invention, the mouth of the clamp is angled upward to match the downward angle of the visor of the headgear. This design causes the sheet to be oriented substantially vertical on an upstanding wearer.

In accordance with an important feature of the invention, the shield also includes a curtain which may be connected to the sides of the shield and wrapped around the back of the neck of the wearer. The curtain hangs down to provide further protection against ultraviolet radiation.

In accordance with another important feature of the invention, at least one spacer is disposed on the inside surface of the sheet to allow air to ventilate from under the attached shield.

Other features and advantages of the present invention will become apparent from the following detailed description, taken in conjunction with the accompanying drawings, which illustrate, by way of example, the principles of the invention.

DETAILED DESCRIPTION OF THE INVENTION

Figures 1, 2:
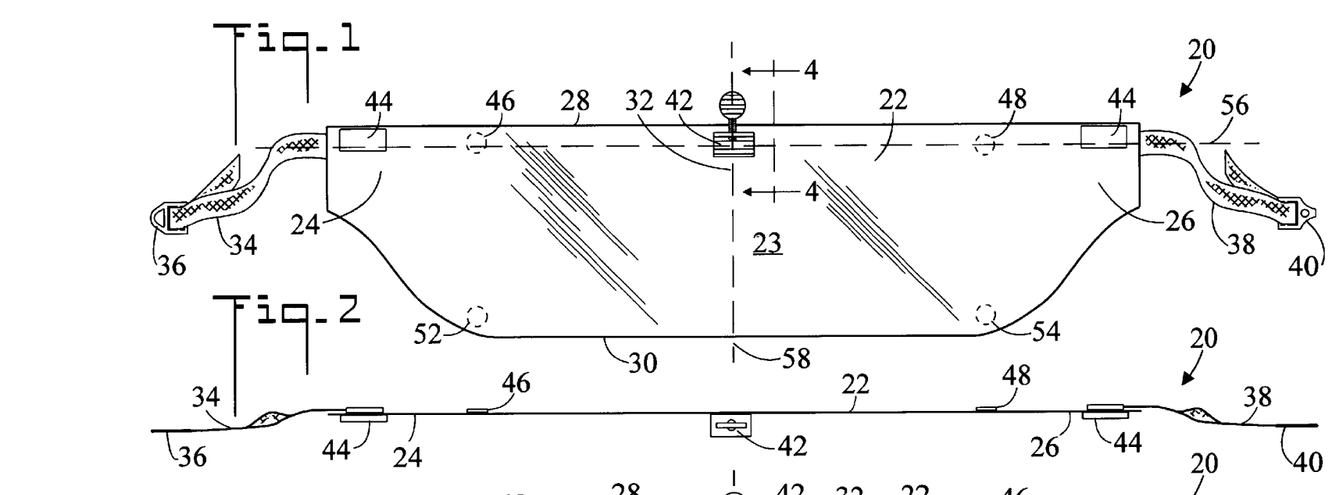
FIG. 1 is a rear elevation view of a headgear mountable shield in accordance with the present invention.
FIG. 2 is a top plan view of the shield.
Figures 3, 4:
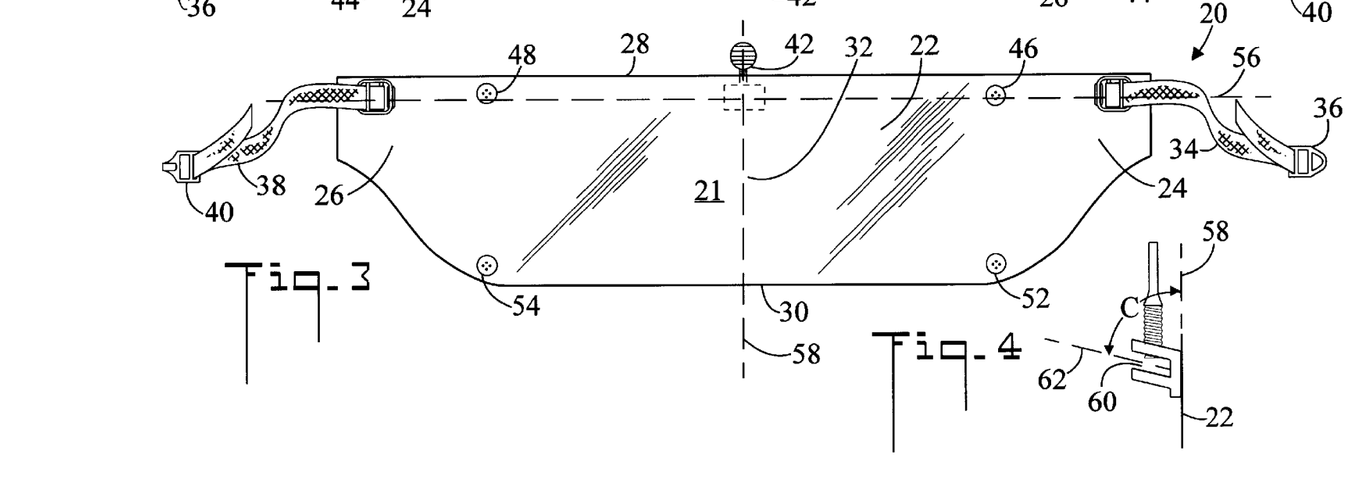
FIG. 3 is a front elevation view of the shield.
FIG. 4 is an enlarged view along the line 4—4 of FIG. 1.
Figure 6:
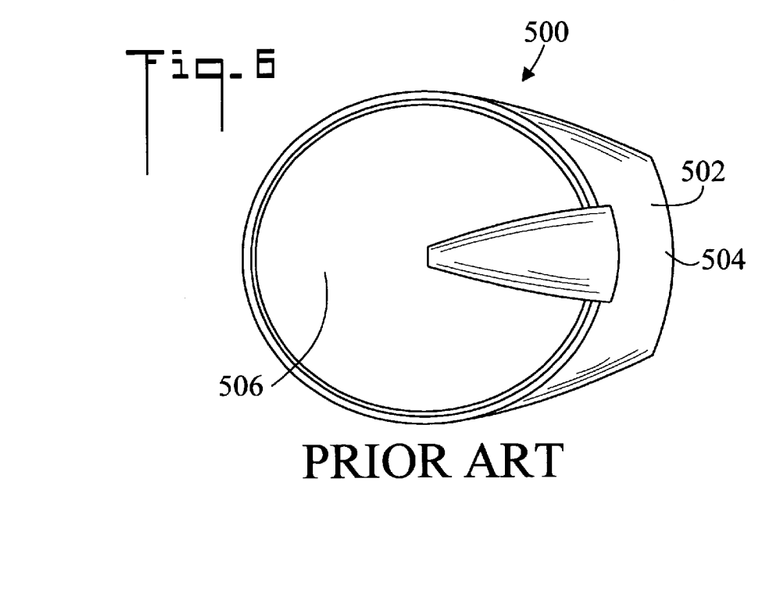
FIG. 6 is a top plan view of the headgear.
Figure 7:
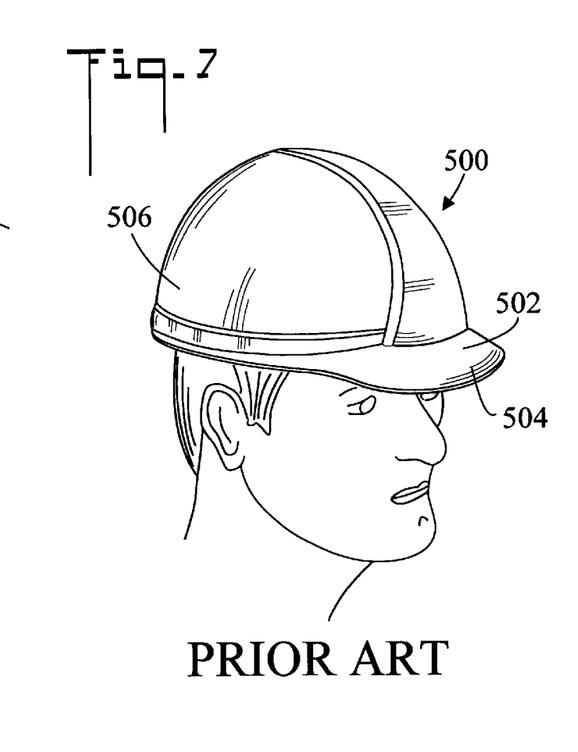
FIG. 7 is a perspective view of the headgear being worn by a wearer.

Referring initially to FIGS. 1–3, there are illustrated rear elevation, top plan, and front elevation views respectively of a headgear mountable shield for protecting a wearer from ultraviolet radiation in accordance with the present invention, generally designated as 20. Also referring to FIGS. 5–7, there are illustrated side elevation, top plan, and perspective views respectively of headgear 500 having visor (bill or brim) 502 having a center portion 504, and a body 506. In the shown embodiment headgear 500 comprises a helmet or hard hat. It may be appreciated however that headgear 500 can include other forms of head coverings such as baseball-type hats, hats having brims, etc.

Shield 20 includes a thin sheet 22 which blocks at least some ultraviolet light and passes at least some visible light. Sheet 22 is shaped and dimensioned to be selectively attachable to the visor 502 and body 506 of headgear 500 in wrap around fashion (also refer to FIG. 10. Sheet has a first end 24, an opposite second end 26, a top edge 28, a bottom edge 30, and a center portion 32. In a preferred embodiment, sheet 22 is fabricated from a sheet of polycarbonate to which has been applied a sheet of tinting material such as is used to tint automobile windows. Such an arrangement can block as much a 99% of ultraviolet radiation. Sheet 22 has an outward facing side 21 and an opposite inward facing side 23. When worn by a wearer, outward facing side 21 is disposed away from the wearer, and inward facing side 23 is disposed toward the wearer (refer also to FIG. 10).

A first flexible elongate member 34 is attached to first end 24, the first flexible elongate member 34 having a free end having a first connector 36. A second flexible elongate member 38 attached to second end 26, the second flexible elongate member 38 having a free end having a second connector 40. First 38 and second 40 connectors are selectively connectable to each other. In a preferred embodiment, first 34 and second 38 elongate members include elastic bands having cooperating connectors which can be stretched around body 506 of headgear 500 (refer also to FIGS. 8–10).

Figure 8:
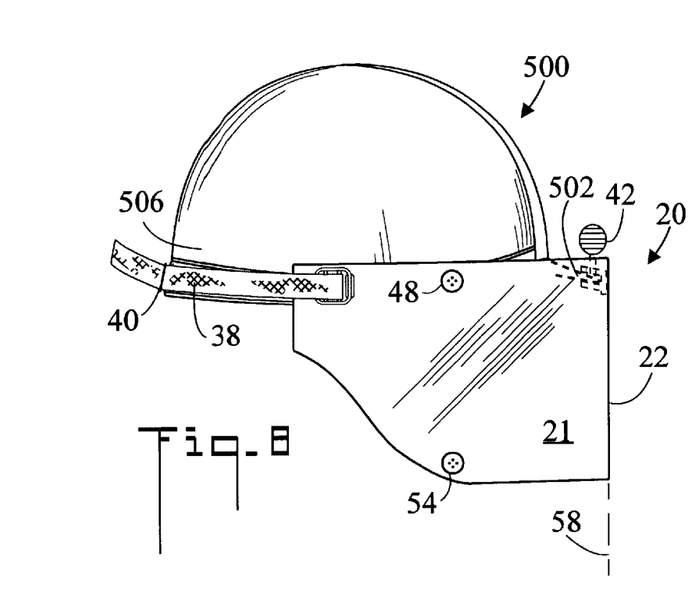
FIG. 8 is a side elevation view of the shield installed on the headgear.
Figure 9:
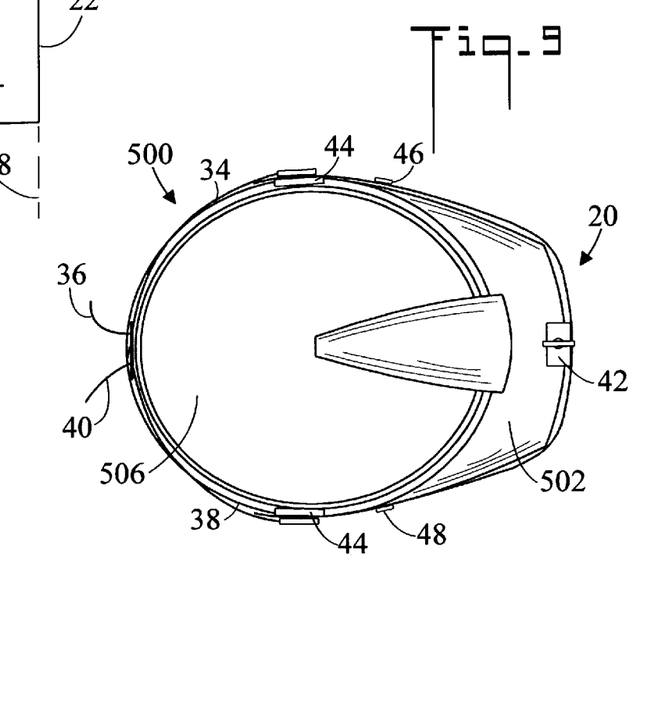
FIG. 9 is a top plan view of the shield installed on the headgear.

Also referring to FIGS. 8 and 9, a clamp 42 is disposed near top edge 28 at center 32 of sheet 22. Clamp 42 is shaped and dimensioned to receive and selectively grasp visor 502 of headgear 500, so that clamp 502 may be fixedly attached to the center 504 of visor 502, first 34 and second 38 flexible elongate members wrapped around the back of body 506 of headgear 500, and first 36 and second 40 connectors connected, thereby attaching shield 20 to headgear 500. In the shown embodiment, clamp 42 includes a screw which abuts visor 502, however it may be appreciated that other forms of clamps could also be employed. In the shown embodiment, one clamp 42 which connects to the center of visor 502 is utilized. It may be appreciated however that multiple clamps 42 could be employed which connect to different locations on visor 502.

At least one spacer 44 is disposed near top edge 28 of inward facing side 23. Spacer 44 creates a slight gap between shield 20 and headgear 500 to ensure proper air circulation. In the shown preferred embodiment, two spacers 44 are disposed at opposite ends 24 and 26 of sheet 22.

Figures 12, 13:
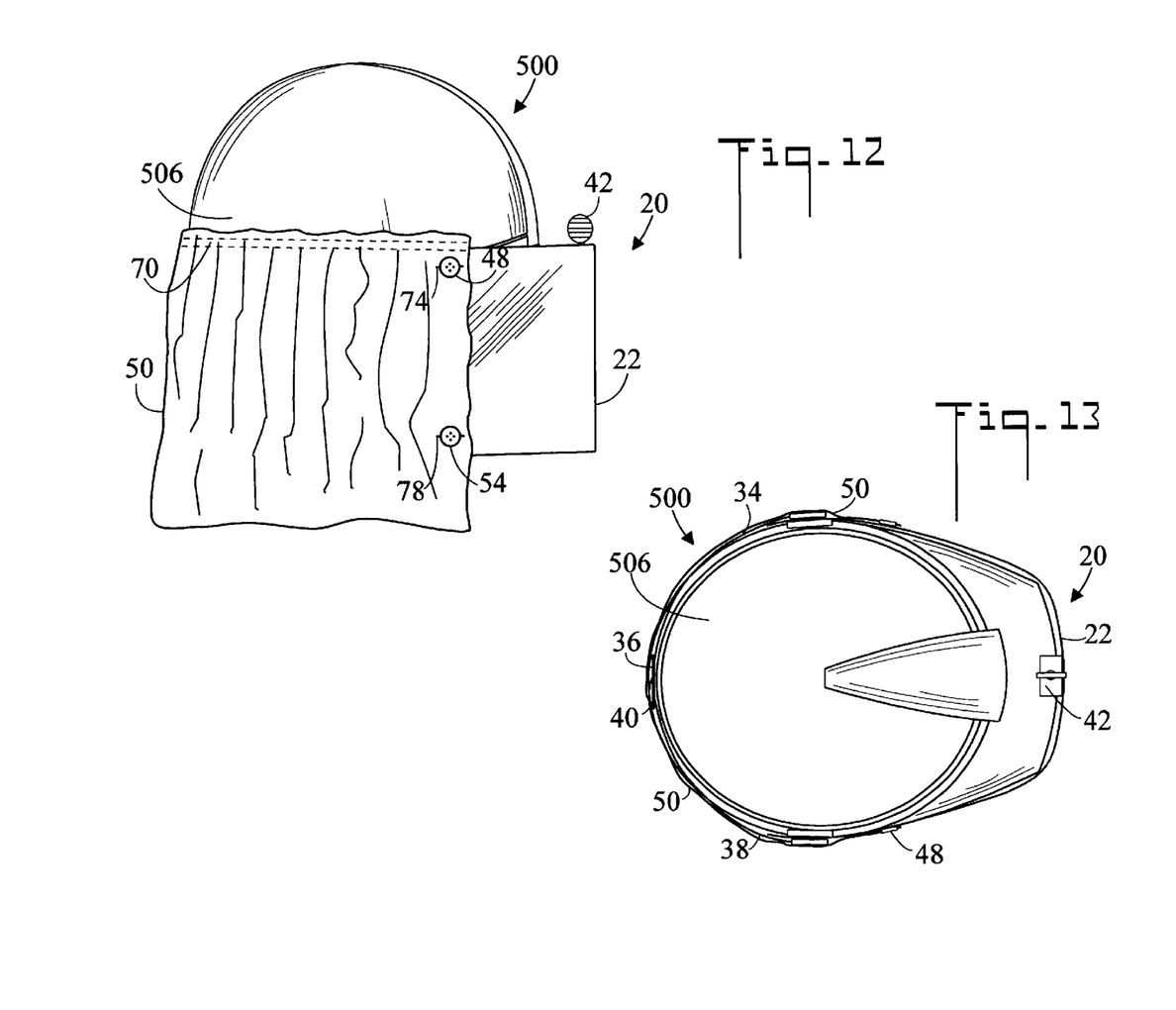
FIG. 12 is a side elevation view of the curtain installed on the shield and headgear.
FIG. 13 is a top plan view of the curtain installed on the shield and headgear.
Figure 14:
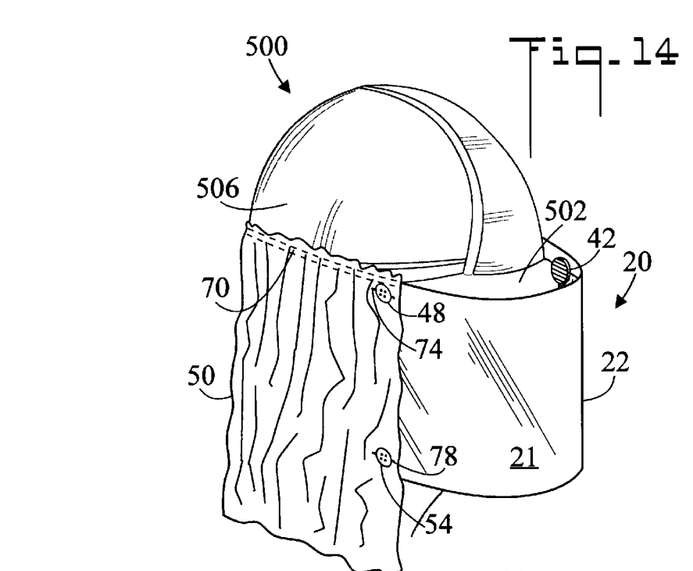
FIG. 14 is a perspective view of the curtain installed on the shield and headgear of a wearer.

Outward facing side 21 has first 46 and second 48 curtain connectors for attaching a curtain 50 to sheet 22 (also refer to FIGS. 12–14). First curtain connector 46 is disposed near top edge 28 and near first end 24 of sheet 22, and second curtain connector 48 is disposed near top edge 28 and near second end 26 of sheet 22. Additionally, outward facing side 21 has third 52 and fourth 54 curtain connectors for attaching curtain 50 to sheet 22. Third curtain connector 52 is disposed near bottom edge 30 and near first end 24 of sheet 22, and fourth curtain connector 54 is disposed near bottom edge 30 and near second end 26 of sheet 22. Sheet 22 has a longitudinal axis 56 and a central transverse axis 58 which is perpendicular to longitudinal axis 56.

Figure 5:
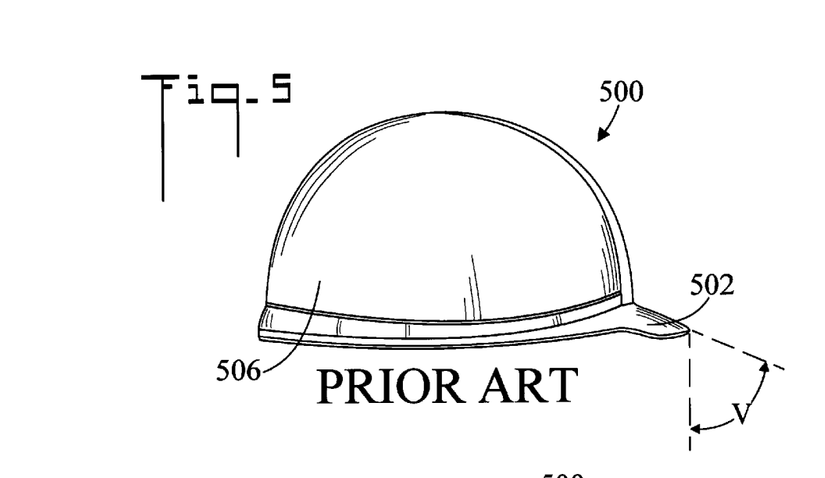
FIG. 5 is a side elevation view of headgear.

FIG. 4 is an enlarged view along the line 4—4 of FIG. 1 showing clamp 42 connected to sheet 22. And, FIG. 5 is a side elevation view of headgear 500. When headgear 500 is installed on an upstanding wearer, visor 502 has a downward angle V. Clamp 42 has a slot 60 for receiving visor 502 of the headgear 500, slot 60 defining an outwardly projecting axis 62. Transverse axis 58 and outwardly projecting axis 62 define an upward acute angle C which substantially equals the downward angle V of visor 502. Because the angles are equal, when shield 20 is installed on headgear 500, transverse axis 58 will be substantially vertical.

Figure 10:
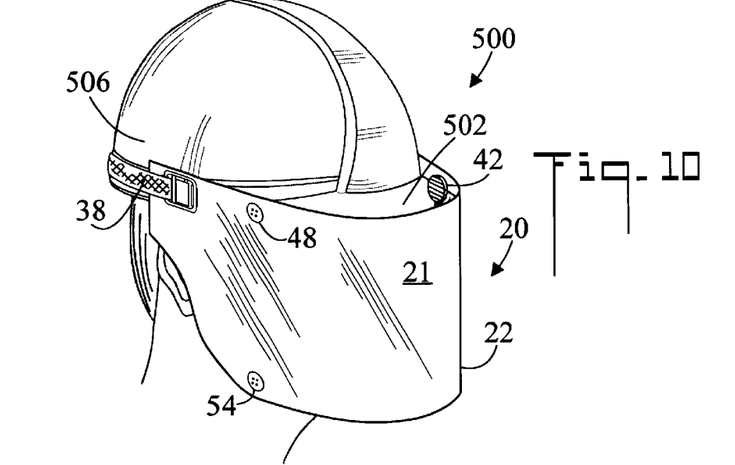
FIG. 10 is a perspective view of the shield installed on the headgear of a wearer.

FIGS. 8–10 are side elevation, top plan, and perspective views of shield 20 installed on headgear 500. Clamp 42 is attached to visor 502, first 34 and second 38 flexible elongate members are wrapped around body 506 of headgear 500, and connectors 36 and 40 connected at the back of headgear 500.

Figure 11:
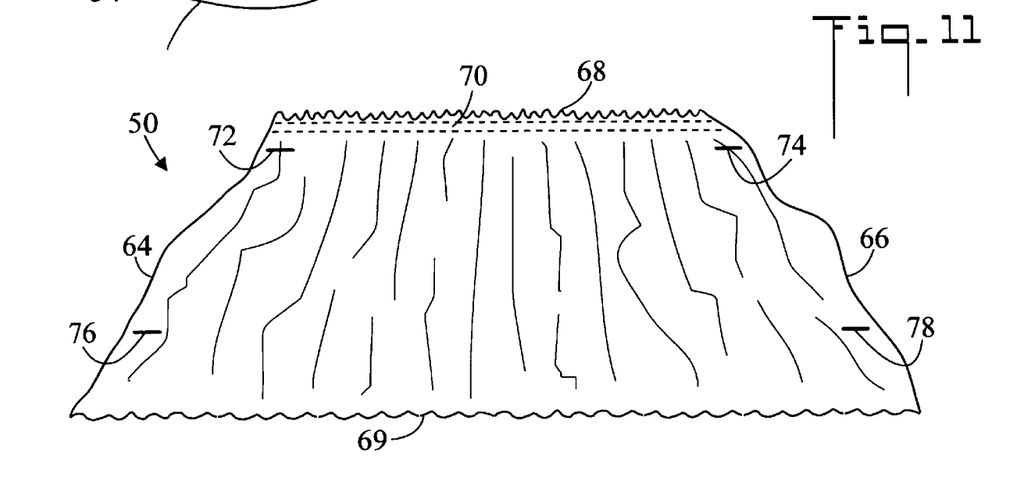
FIG. 11 is a side elevation view of a curtain.

Referring now to FIG. 11, there is illustrated a side elevation view of a curtain 50. Curtain 50 is typically fabricated from opaque fabric or other flexible material, and has a first end 64, an opposite second end 66, a top side 68, and an opposite bottom side 69. Elastic 70 is disposed along top side 68. A first connection means 72 is disposed near first end 64 and top side 68 of curtain 50, and a second connection means 74 is disposed near second end 66 and top side 68 of curtain 50. First connection means 72 is selectively connectable to first curtain connector 46, and second connection 74 means is selectively connectable to second curtain connector 48. In the shown embodiment, first 72 and second 74 connection means are button holes which cooperate with first 46 and second 48 curtain connectors which are buttons attached to sheet 22. It may be appreciated however that, the curtain connectors of sheet 22 and the connection means of curtain 50 could include other devices such as clasps, hook and loop fasteners, snaps, etc.

Third connection means 76 are disposed near first end 64 and bottom side 69 of curtain 50, and fourth connection means 78 are disposed near second end 66 and bottom side 69 of curtain 50. Third connection means 76 are selectively connectable to third curtain connector 52 of sheet 22, and fourth connection means 78 are selectively connectable to fourth curtain connector 54 of sheet 22. By having curtain connections on the lower portion of sheet 22, curtain 50 is held fixedly in place with respect to sheet 22, and not subject to displacement by the wind or other force.

FIGS. 12–14 are side elevation, top plan, and perspective views respectively of curtain 50 installed on shield 20 and headgear 500. Curtain 50 has been selectively and elastically wrapped around (a) body 506 of the headgear 500 and (b) the connected first and second elongate flexible members 34 and 38. When so connected, curtain 50 comprises a downwardly hanging veil which protects the sides and back of the neck of the wearer.

Figure 15:
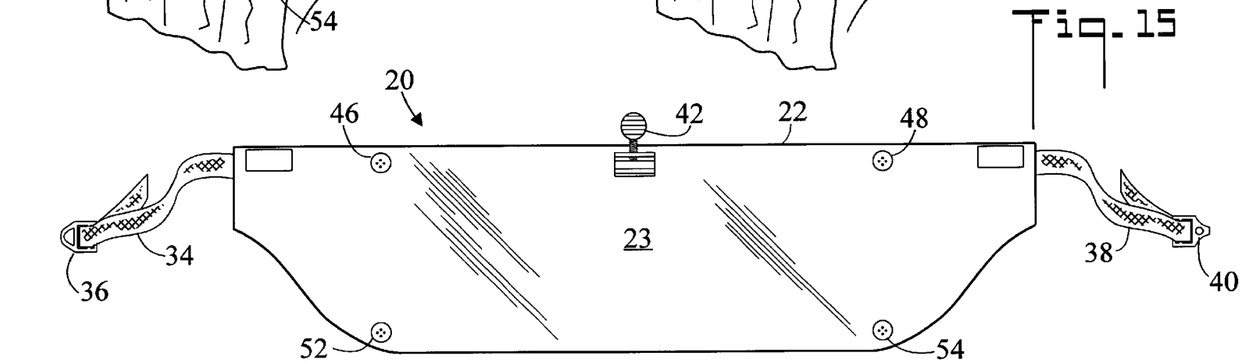
FIG. 15 is a rear elevation view of a second embodiment of the shield and curtain; and, FIG. 16 is a perspective view of the curtain installed on the second embodiment shield and the headgear.

FIG. 15 is a rear elevation view of a second embodiment of shield 20 and curtain 50. This embodiment is identical to the embodiment of FIGS. 1–4 with the exception that first 46, second 48, third 52, and fourth 54 curtain connectors are disposed in the same relative position on inward facing side 23 rather than on outward facing side 21. In this fashion, curtain 50 is selectively and elastically wrappable around body 506 of headgear 500, and first through fourth connection means attached to first through fourth curtain connectors respectively, so that curtain 50 resides inside rather than outside shield 20.

Figure 16:
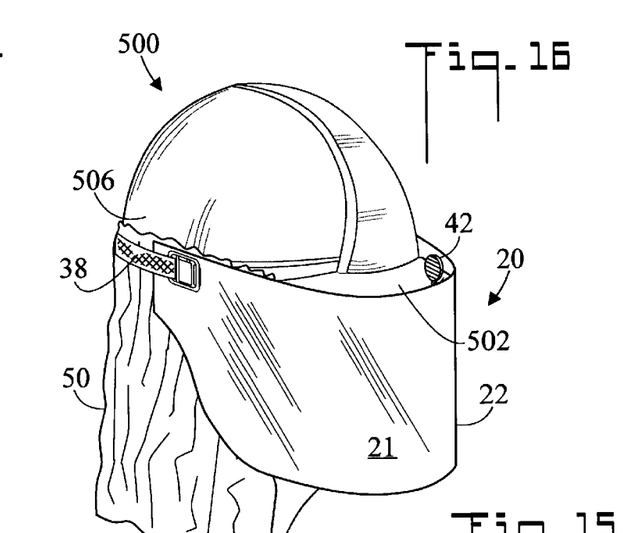

FIG. 16 is a perspective view of curtain 50 installed on the second embodiment shield 20 and headgear 500. It may be observed that in this embodiment shield 20 serves to retain curtain 50 in place on the wearer.

In terms of used, a method for protecting a person from ultraviolet radiation, comprises:

(1) providing headgear 500 having (a) a visor 502 having a center 504, and (b) a body 506;

(2) providing a shield 20 including:
  a sheet 22 which blocks at least some ultraviolet light and passes at least some visible light, the sheet 22 is shaped and dimensioned to be selectively attachable to the visor 502 and the body 506 of the headgear 500 in wrap around fashion,
  the sheet 22 has a first end 24, an opposite second end 26, a top edge 28, a bottom edge 30, and a center 32;
  a first flexible elongate member 34 attached to first end 24, the first flexible elongate member 34 having a free end having a first connector 36;
  a second flexible elongate member 38 attached to second end 26, the second flexible elongate member 38 having a free end having a second connector 40, the first 36 and second 40 connectors selectively connectable to each other; and,
  a clamp 42 is disposed near top edge 28 at center 32 of sheet 22, the clamp 42 is shaped and dimensioned to receive and selectively grasp visor 502 of headgear 500;

(3) fixedly attaching clamp 42 to center 504 of visor 502;

(4) wrapping first 34 and second 38 elongate members around body 506 of headgear 500;

(5) connecting first 36 and second 40 connectors together, so that shield 20 is attached to headgear 500; and, (6) the person placing headgear 500 and attached shield 20 upon the person's head.

The method further including:

(7) the sheet 22 also having:
  an outward facing side 21;
  the outward facing side 21 having first 46 and second 48 curtain connectors for attaching curtain 50 to sheet 22, the first curtain connector 46 disposed near top edge 28 and near first end 24 of sheet 22, and the second curtain connector 48 disposed near top edge 28 and near second end 26 of sheet 22;

(8) providing a curtain 50 having:
  a first end 64, an opposite second end 66, and a top side 68;
  elastic 70 disposed along top side 68;
  first connection means 72 disposed near first end 64 and top side 68 of curtain 50;
  second connection means 74 disposed near second end 66 and top side 68 of curtain 50;

(9) wrapping curtain 50 around (a) body 506 of headgear 500 and (b) the connected first 34 and second 38 elongate flexible members;

(10) connecting first connection means 72 to first curtain connector 46; and, (11) connecting second connection means 74 to second curtain connector 48, wherein curtain 50 forms a downwardly hanging veil.

The preferred embodiments of the invention described herein are exemplary and numerous modifications, dimensional variations, and rearrangements can be readily envisioned to achieve an equivalent result, all of which are intended to be embraced within te scope of the appended claims.

I claim:

1. A headgear mountable shield for protecting a wearer from ultraviolet radiation, the headgear having (a) a visor having a center, and (b) a body, said shield comprising:

a sheet which blocks at least some ultraviolet light and passes at least some visible light, said sheet shaped and dimensioned to be selectively attachable to the visor and body of the headgear in wrap around fashion;

said sheet having a first end, an opposite second end, a top edge, a bottom edge, and a center;

a first flexible elongate member attached to said first end, said first flexible elongate member having a free end having a first connector;

a second flexible elongate member attached to said second end, said second flexible elongate member having a free end having a second connector, said first and second connectors selectively connectable to each other; and, a clamp disposed near said top edge at said center of said sheet said clamp shaped and dimensioned to receive and selectively grasp the visor of the headgear, so that said clamp may be fixedly attached to the center of the visor, said first and second flexible elongate members wrapped around the body of the headgear, and said first and second connectors connected, thereby attaching said shield to the headgear.

2. A shield according to claim 1, when the headgear is installed on an upstanding wearer, the visor having a downward angle, said shield further including:

said sheet having a longitudinal axis and a transverse axis perpendicular to said longitudinal axis;

said clamp having a slot for receiving the visor of the headgear, said slot defining an outwardly projecting axis;

said transverse axis and said outwardly projecting axis defining an acute angle which substantially equals the downward angle of the visor; and, so that when said shield is installed on the headgear, said transverse axis is substantially vertical.

3. A shield according to claim 1, further including:

a curtain having a first end, an opposite second end, and a top side;

elastic disposed along said top side;

first connection means disposed near said first end and said top side of said curtain;

second connection means disposed near said second end and said top side of said curtain;

said sheet having an outward facing side;

said outward facing side having first and second curtain connectors for attaching said curtain to said sheet, said first curing connector disposed near said top edge and near said first end of said sheet, and said second curtain connector disposed near said top edge and near said second end of said sheet;

said curtain selectively elastically wrappable around (a) the body of the headgear and (b) the connected first and second elongate flexible members;

said first connection means selectively connectable to said first curtain connector;

said second connection means selectively connectable to said second curtain connector; and, wherein when so connected, said curtain forming a downwardly hanging veil.

4. A shield according to claim 3, further including:

third connection means disposed near said first end and a bottom side of said curtain;

fourth connection means disposed near said second end and said bottom side of said curtain;

said outward facing side having third and fourth curtain connectors for attaching said curtain to said sheet, said third curtain connector disposed near said bottom edge and near said first end of said sheet, and said fourth curtain connector disposed near said bottom edge and near said second end of said sheet;

said third connection means selectively connectable to aid third curtain connector; and, said fourth connection means selectively connectable to said fourth curtain connector.

5. A shield according to claim 1, further including:

a curtain having a first end, an opposite second end, a top side, and an opposite bottom side;

elastic disposed along said top side;

first connection means disposed near said first end and said top side of said curtain;

second connection means disposed near said second end and said top side of said curtain;

said sheet having an inward facing side;

said inward facing side having first and second curtain connectors for attaching said curtain to said sheet, said first curtain connector disposed near said top edge and near said first end of said sheet, and said second curtain connector disposed near said top edge and near said second end of said sheet;

said curtain selectively elastically wrappable around the body of the headgear; said first connection means selectively connectable to said first curtain connector;

said second connection means selectively connectable to said second curtain connector; and, wherein when so connected, said curtain forming a downwardly hanging veil.

6. A shield according to claim 5, further including:

third connection means disposed near said first end and said bottom side of said curtain;

fourth connection means disposed near said second end and said bottom side of said curtain;

said inward facing side having third and fourth curtain connectors for attaching said curtain to said sheet, said third curtain connector disposed near said bottom edge and near said first end of said sheet, and said fourth curtain connector disposed near said bottom edge and near said second end of said sheet;

said third connection means selectively connectable to said third curtain connector; and, said fourth connection means selectively connectable to said fourth curtain connector.

7. A shield according to claim 1, further including:

said sheet having an outward facing side and an opposite inward facing side;

at least one spacer is disposed near said top edge of said inward facing side.

8. A shield according to claim 1, further including:

said sheet including a sheet of polycarbonate to which is applied a sheet of tinting material.

9. A shield according to claim 1, when the headgear is installed on an upstanding wearer, the visor having a downward angle, said shield further including:

said sheet having a longitudinal axis and a transverse axis perpendicular to said longitudinal axis;

said clap having a slot for receiving the visor of the headgear, said slot defining an outwardly projecting axis;

said transverse axis and said outwardly projecting axis defining an acute angle which substantially equals the downward angle of the visor, so that when said shield in installed on the headgear, said transverse axis is substantially vertical;

a curtain having a first end, an opposite second end, a top side, and an opposite bottom side;

elastic disposed along said top side;

first connection means disposed near said first end and said top side of said curtain;

second connection means disposed near said second end and said top side of said curtain;

said sheet having an outward facing side;

said outward facing side having first and second curtain connectors for attaching said curtain to said sheet, said first curtain connector disposed near said top edge and near said first end of said sheet, and said second curtain connector disposed near said top edge and near said second end of said sheet;

said curtain selectively elastically wrappable around (a) the body of the headgear and (b) the connected first and second elongate flexible members;

said first connection means selectively connectable to said first curtain connector;

said second connection means selectively connectable to said second curtain connector;

wherein when so connected, said curtain forming a downwardly hanging veil;

third connection means disposed near said first end and said bottom side of said curtain;

fourth connection means disposed near said second end and said bottom side of said curtain;

said outward facing side having third and fourth curtain connectors for attaching said curtain to said sheet, said third curtain connector disposed near said bottom edge and near said first end of said sheet, and said fourth curtain connector disposed near said bottom edge and near said second end of said sheet;

said third connection means selectively connectable to said third curtain connector; and, said fourth connection means selectively connectable to said fourth curtain connector.

10. A method for protecting a person from ultraviolet radiation, comprising:

(1) providing headgear having (a) a visor having a center, and (b) a body;

(2) providing a shield including:
  a sheet which blocks at least some ultraviolet light and passes at least some visible light said sheet shaped and dimensioned to be selectively attachable to said visor and said body of said headgear in wrap around fashion,
  said sheet having a first end, an opposite second end, a top edge, a bottom edge, and a center;
  a first flexible elongate member attached to said first end, said first flexible elongate member having a free end having a first connector;
  a second flexible elongate member attached to said second end, said second flexible elongate member having a free end having a second connector, said first and second connectors selectively connectable to each other; and,
  a clamp disposed near said top edge at said center of said sheet, said clamp shaped and dimensioned to receive and selectively grasp said visor of said headgear;
(3) fixedly attaching said clamp to said center of said visor;
(4) wrapping said first and second elongate members around said body of said headgear;
(5) connecting said first and second connectors together, so that said shield is attached to said headgear; and,
(6) the person placing said headgear and attached said shield upon the person's head.

11. The method according to claim 10, further including:
(7) providing a curtain having:
  a first end, an opposite second end, and a top side;
  elastic disposed along said top side;
  first connection means disposed near said first end and said top side of said curtain;
  second connection means disposed near said second end arid said top side of said curtain;
(8) said sheet also having:
  an outward facing side;
  said outward facing side having first and second curtain connectors for attaching said curtain to said sheet, said first curtain connector disposed near said top edge and near said first end of said sheet, and said second curtain connector disposed near said top edge and near said second end of said sheet;
(9) wrapping said curtain around (a) said body of said headgear and (b) said connected first and second elongate flexible members;
(10) connecting said first connection means to said first curtain connector; and,
(11) connecting said second connection means to said second curtain connector, wherein said curtain forms a downwardly hanging veil.

12. A headgear mountable shield for protecting a wearer from ultraviolet radiation, the headgear having a visor and a body, said shield comprising:
  a thin sheet which blocks at least some ultraviolet light and passes at least some visible light, said sheet shaped and dimensioned to be selectively attachable to the visor and body of the headgear in wrap around fashion;
  said sheet having a fist end, an opposite second end, a top edge, a bottom edge, and a center;
  a first flexible elongate member attached to said first end, said first flexible elongate member having a free end having a first connector;
  a second flexible elongate member attached to said second end, said second flexible elongate member having a free end having a second connector, said first and second connectors selectively connectable to each other; and,
  a clamp disposed near said top edge of said sheet, said clamp shaped and dimensioned to receive and selectively grasp the visor of the headgear, so that said clamp may be fixedly attached to the visor, said first and second flexible elongate members wrapped around the body of the headgear, and said first and second connectors connected, thereby attaching said shield to the headgear.

* * * * *